United States Patent [19]

Katsoyannis

[11] Patent Number: 5,208,217
[45] Date of Patent: May 4, 1993

[54] HEPATOSPECIFIC INSULIN ANALOGUES

[75] Inventor: Panayotis G. Katsoyannis, Manhassett, N.Y.

[73] Assignee: Mount Sinai School of Medicine of The City University of New York, New York, N.Y.

[21] Appl. No.: 785,146

[22] Filed: Oct. 29, 1991

Related U.S. Application Data

[63] Continuation of Ser. No. 340,929, Apr. 20, 1989, abandoned.

[51] Int. Cl.$^5$ .................. A61K 37/26; C07K 7/40
[52] U.S. Cl. ........................ 514/3; 530/303
[58] Field of Search .................. 514/3; 530/303

[56] References Cited

U.S. PATENT DOCUMENTS

| | | | |
|---|---|---|---|
| 3,420,810 | 1/1969 | Katsoyannis et al. | |
| 4,421,685 | 12/1983 | Chance et al. | 514/3 |
| 4,430,266 | 2/1984 | Frank | 514/3 |
| 4,459,226 | 7/1984 | Grimes et al. | 514/3 |
| 4,569,791 | 2/1986 | Frank et al. | 514/3 |
| 4,569,792 | 2/1986 | Frank et al. | 514/3 |
| 4,581,165 | 8/1986 | Frank et al. | 514/3 |
| 4,652,547 | 3/1987 | Chance et al. | 514/4 |
| 4,652,548 | 3/1987 | Chance et al. | 514/4 |
| 4,946,828 | 8/1990 | Markussen | 514/3 |

FOREIGN PATENT DOCUMENTS 0214826  3/1987  European Pat. Off.

OTHER PUBLICATIONS

Chemical Abstracts, vol. 94, p. 623, 94:47733x, Danho et al.
Proc. of the Nat. Acad. of Sciences of the USA 86 (1989) No. 2, pp. 458-461.
Ohta et al., J. Protein Chemistry, 7: 55-65 (1988).
Danho, W. et al., Hoppe-Seyler's Z. Physiol. Chemie., 361(5): 747-754, 1980.
Botstein, D. et al., Science, vol. 229, pp. 1193-1201. (1985).
Blake, J. et al., Proc. Natl. Acad. Sci USA 80, pp. 1556-1559 (1986).
Smith, In Vitro Mutagenesis, Annual Review of Genetics, vol. 19, pp. 423-462, (1985).
Chance, R. E., et al. Pept., Proc. Amer, Pept. Symp. 7th., pp. 721-728 (1981).
Katsoyannis, P. G., et al., Journal of the American Chemical Society, 88, 166 (1966).
Kitagawa, K., et al., Biochemistry 23, pp. 1405-1413 4444-4448 (1984).
Schwatz, G. P. et al., Int. J. Peptide Protein Res. 17, pp. 243-255 (1981).
Katsoyannis, P. G. et al., Proceedings of the Natl. Acad. of Sciences, vol. 55, No. 6, pp. 1554-1561 (1966).
Schwartz, G. P. et al., Journal of the Chemical Society, Perkins Transactions I (1973).
Schwartz, G. P. Journal of The Chemical Society, Perkin Transactions I (1973).
Chan S. J., et al., Proc. Natl. Acad., Sci, USA, vol. 84, pp. 2194-2197, (1987).
Katsoyannis, P. G., et al., Biochemistry, v, pp. 2635-2642, 2656-2668 (1967).
Katsoyannis, P. G. et al., Biochemistry, 6, pp. 2642-2655 (1967).
Katsoyannis, P. G. et al., Biochemistry, v. pp. 2656-2668, (1967).
Schwartz, G. et al., Biochemistry, 15, pp. 4071-4076 (1976).

(List continued on next page.)

*Primary Examiner*—Lester L. Lee
*Attorney, Agent, or Firm*—Brumbaugh, Graves, Donohue & Raymond

[57] ABSTRACT

New insulin analogues have now been synthesized and found to be hepatospecific. These insulin analogues contain substitutions for one or more amino acids in the A and B chains. Specifically, tryptophan or other bulky, hydrophobic residues are substituted at the A13, A14, A15, A19 and B16 positions of the insulin polypeptide to produce the hepatospecific insulin analogues of the claimed invention.

14 Claims, 4 Drawing Sheets

OTHER PUBLICATIONS

Schwartz et al., J. Chem. Research (M), pp. 2453–2466, (1977).

Schwartz G. P. et al. Journal of Chem. Res. (S) pp. 220–221, (1977).

Katsoyannis, P. G., Structure and Function Relationships In Insulin: A Synthetic Approach, Elsevier North Holland, Inc. pp. 171–192 (1980).

Katsoyannis, P. G., New Synthetic Insulins, Treatment of Early Diabetes, pp. 319–328 (1979).

Burke, G. T. et al. Int. J. Peptide Protein Res., 23, pp. 394–401, (1984).

Schwartz, G., Journal of Protein Chemistry, vol. 1, No. 3, pp. 177–189, (1982).

Ferderigos, N., Int. J. Peptide Protein Res. 13, pp. 43–53, (1979).

Cosmatos, A., et al., Int. J. Peptide Protein Res. 14, pp. 457–471, 1979.

Schwartz, G. et al., Biochemistry, 17, pp. 4550–4556 (1978).

Ferderigos, N., et al. Journal of Protein Chemistry, vol. 2, pp. 147–170, (1983).

Schwartz, G. et al., Biochemistry vol. 22 pp. 4561–4567 (1983).

Field et al., "Role of Liver in Insulin physiology" Diabetes Care 3:255–260 (1980).

Proc. Natl. Acad. Sci, US, vol. 84, Sep. 1987 (US) G. P. Schwartz et al.: "A Superactive insulin": [B10–asparatic Acid] insulin (human), pp. 6408–6411.

Chemical Abstracts, vol. 105, 1986, M. Bajaj et al.: "Coypu insulin. Primary structure, conformation and biological properties of a hystricomorph rodent insulin", see p. 87 abstract No. 184142p.

Chemical Abstracts, vol. 101, 1984, G. T. Burke et al.: "Nature of the B10 amino acid residue. Requirements for high biological activity of insulin" see p. 72, abstract No. 84120d.

HEPATOSPECIFIC INSULIN ANALOGUES

This invention was made with government support under grant #DK-12925 awarded by the National Institutes of Health. The government has certain rights in the invention.

This application is a continuation of application Ser. No. 07/340,929, filed on Apr. 20, 1989, now abandoned.

BACKGROUND OF THE INVENTION

The present invention relates to novel insulin analogues and their use in pharmaceutical compositions for the treatment of diabetes.

Insulin is a hormone which has a key role in the regulation of growth and metabolism in vertebrates. Severe metabolic derangements occur in the absence of insulin resulting from the failure of many cells to utilize glucose and amino acids normally. The inability to metabolize glucose leads in man to diabetes mellitus, a complex chronic metabolic disorder in which there is abnormal carbohydrate, fat and protein metabolism. In its most fully expressed clinical form, diabetes mellitus is characterized by an absolute or relative deficiency of insulin or insulin activity and is associated with glucosuria, ketonuria, growth arrest, and negative nitrogen balance. These conditions can ultimately lead to death from acute metabolic acidosis caused by unrestrained oxidation of fatty acids or inanition which results from the lack of sufficient lipid reserves needed to generate ketone bodies. Inanition is defined as a condition characterized by marked weakness, extreme weight loss, and a decrease in metabolism resulting from prolonged and severe insufficiency of food. *Dorland's Illustrated Medical Dictionary*, 25th Edition.

The discovery and purification of insulin in the 1920's and its association with diabetes mellitus provided the means to intervene in the disease. See, e.g., Bliss, *The Discovery of Insulin* (1983), University of Chicago Press, Chicago, Ill. Today, insulin administration to diabetic patients is the primary therapeutic means for controlling the disease.

Insulin is a ca 6000 dalton polypeptide which is composed of two short peptide chains, termed A and B, which are linked to each other by invariant disulfide bridges. In almost all insulins studied, the A chain, which is 21 amino acids long, also contains an internal disulfide bridge. The B chain is 30 amino acids in length. Like many eukaryotic proteins, insulin is synthesized in a precursor form which is post-synthetically processed to the mature two polypeptide chain active hormone.

The immediate precursor of insulin is proinsulin, a single chain polypeptide composed of the B and A chains linked to a connecting peptide of approximately 31 amino acids, termed the C-peptide, by adjacent pairs of basic residues. The order of the three peptides in the proinsulin molecule is $NH_2$-B chain-Arg-Arg-C-peptide-Lys-Arg-A chain-COOH. The translation product of insulin mRNA, however, is preproinsulin which is proinsulin that contains at its $NH_2$ terminus a 24 amino acid largely hydrophobic signal peptide characteristic of proteins that are either transported through or inserted into cellular membranes.

Preproinsulin is synthesized in pancreatic beta cells located within the islets of Langerhans which are dispersed throughout the pancreas. Removal of the signal peptide occurs in the rough endoplasmic reticulum with the resulting fully folded oxidized proinsulin being transported to the Golgi apparatus for packaging into secretion granules. The folded proinsulin is stabilized by disulfide bonds. During maturation of the secretion granules, the folded proinsulin molecule is cleaved by specific proteases at the paired basic residues to liberate insulin and the C-peptide.

As discussed above, therapy for diabetes mellitus includes administration of controlled amounts of insulin to the diabetic patient. The insulin so administrated has, for the most part, been obtained from animal pancreases, notably bovine and porcine. Bovine and porcine insulins function to maintain hormonal homeostasis in the same way as human insulin with about the same potency but, because they are foreign proteins, can elicit an immunological response which diminishes their usefulness. More recently, human insulin, generated by recombinant DNA techniques, has been added to the therapeutic armamentarium. The use of human insulin, produced by recombinant DNA or other techniques, is not likely to produce the adverse immunological problems attendant the use of animal insulins. Even with the availability of natural human insulin, however, administration of the hormone to diabetics has not been always sufficient to restore normal metabolism. There is thus a need for alternative insulins with better activity or other means of therapy for diabetes.

U.S. application Ser. No. 074,558 discloses a superactive human insulin analogue, [10-Aspartic Acid-B] human insulin, which has increased activity over natural human insulin. Specifically, [10-Aspartic Acid-B] human insulin was determined to be 4 to 5 times more potent than natural insulins. U.S. application Ser. No. 273,957 and International Application Serial No. PCT/US88/02289 disclose other superactive insulin analogues, des-pentapeptide (B26-B30)-[$Asp^{B10}$, $Tyr^{B25}$-α-carboxamide] human insulin, (B26-B30)-[$Glu^{B10}$, $Tyr^{B25}$-α-carboxamide] human insulin, and further insulin analogs of the formula des(B26-B30)-[$X^{B10}$, $Tyr^{B25}$-α-carboxamide] human insulin, in which X is a residue substituted at position 10 of the B chain. These insulin analogues have potencies anywhere from 11 to 20 times that of natural human insulin. All of the above-described insulin analogues involve amino acid substitutions along the A or B chains of natural human insulin, which increase the potency of the compound or change other properties of the compound.

None of the current insulin delivery routes of natural insulin and known insulin analogues exactly mimic insulin secretion from the normal pancreas. Normally, insulin enters the splanchnic venous circulation, thereby exposing the liver to higher concentrations of insulin than those to which peripheral tissue is exposed. With standard subcutaneous administration of insulin, plasma glucose concentrations may be normalized, but glucose recycling and the production and utilization of protein and lipids may not be. In addition, peripheral vascular tissues are exposed to higher than normal insulin concentrations. Although the long-term effects of these metabolic abnormalities remains to be defined, there is considerable evidence that peripheral hyperinsulinemia may be a significant risk factor for the development of atherosclerosis.

Hepatospecific insulin analogues, or those which are more active in the liver than in adipose tissue, offer several advantages over currently available insulin therapy. Using such analogues it may be possible to obtain preferential hepatic uptake during peripheral subcutaneous administration, thereby mimicking more closely the metabolic balance between the liver and peripheral tissues. Although attempts to mimic this pattern with intraperitoneal injection of insulin have been undertaken, this technique has the potential disadvantages of difficultly for intraperitoneal access and risk of peritonitis. Hepatospecific insulin achieves the same effect as intraperitoneal insulin, without these increased risks.

SUMMARY OF THE INVENTION

New insulin analogues have now been synthesized and found to be hepatospecific. These insulin analogues contain substitutions for one or more amino acids in the A and B chains. Specifically, tryptophan or other bulky, hydrophobic residues are substituted at the A14 and A19 positions of the insulin polypeptide to produce the hepatospecific insulin analogues of the claimed invention. It is believed that tryptophan or other bulky hydrophobic residues inserted at the A13, A15 and B16 positions will also lead to hepatospecific insulin analogues.

The invention also relates to pharmaceutical compositions for the treatment of diabetes in patients needing such treatment which comprise a therapeutically effective amount of an insulin analogue according to the claimed invention together with a pharmaceutically acceptable carrier.

Furthermore the invention relates to a method for treating diabetes comprising administering to a diabetic patient in need of insulin therapy a therapeutically effective amount of a human insulin analogue according to the claimed invention together with a pharmaceutically acceptable carrier.

DESCRIPTION OF THE INVENTION

The claimed invention relates to an insulin analogue having an A chain comprising amino acids A1 through A21 and a B chain comprising amino acids B1 through B30, in which the A14 amino acid is substituted with an amino acid residue selected from the group consisting of tryptophan, naphthylalanine, N$\gamma$-dansyl-a,$\gamma$-diaminobutyric acid, leucine, valine, phenylalanine, and other hydrophobic amino acids. The claimed invention also relates to an insulin analogue having an A chain comprising amino acids A1 through A21 and a B chain comprising amino acids B1 through B30, in which an amino acid residue selected from the group consisting of tryptophan, naphthylalanine, N$\gamma$-dansyl-a,$\gamma$-diaminobutyric acid, leucine, valine, phenylalanine, and other hydrophobic amino acids is substituted for an amino acid selected from the group consisting of the A13 amino acid, the A14 amino acid, the A15 amino acid, the A19 amino acid, the B16 amino acid, and combinations thereof.

The claimed invention further relates to an insulin analogue, [Trp$^{14}$-A] insulin, having the formula The term insulin analogue refers to a protein which has the basic A chain and B chain structure of human (and other species of) insulin and contains all of the half cysteine residues in the same position as present in native insulin. Thus, insulin analogues retain the disulfide bridge arrangement of natural insulins. Useful insulin analogues can differ from native insulins by the addition, deletion, substitution or modification of one or more amino acids in one or both chains of the molecule, but must retain at least some portion of insulin potency. See e.g. Katsoyannis, *Treatment of Early Diabetics* (1979), pp. 319-327, Plenum Publ. Corp.; Blondell, Adv. Prot. Chem. (1972), vol. 26, pp. 330-362.

The insulin analogues of the invention, which differ from natural insulin by the substitutions of tryptophan for the naturally-occurring amino acid at positions A14 and A19 were unexpectedly found to have higher potency in hepatic cells than in adipose tissue. It is also believed that insulin analogues which differ from natural insulin by the substitution of naphthylalanine, N$\gamma$-dansyl-a, $\gamma$-diaminobutyric acid, leucine, valine, phenylalanine and other hydrophobic amino acids for the naturally occurring amino acids at positions A13, A15 and B16 may also have higher potency in hepatic cells than in adipose tissue.

The most important property of these insulin analogues is their hepatospecifity whereby they are more active in the liver than in the adipose tissue or peripheral tissue. For example, in adipose tissue [Trp$^{14}$-A] insulin displays an activity of about 60% of that of natural insulin (lipogenesis assay) whereas in the liver exhibits an activity (in terms of inhibiting gluconeogenesis) of 90% of that of natural insulin. It should be noted that whereas insulin stimulates the utilization of glucose in the peripheral tissue (i.e., adipose tissue), in the liver insulin inhibits the de novo synthesis of glucose (inhibition of gluconeogenesis).

It is believed that substitution of the A14 amino acid residue in the molecule of insulin with other bulky residues such as naphthylalanine or Nγ-dansyl-a,γ-diaminobutyric acid or other hydrophobic amino acid residues such as leucine, valine, or phenylalanine also leads to hepatospecific insulin analogues.

Furthermore, it is also believed that single amino acid insertions at the A13, A15, or B16 positions of the insulin polypeptide or double insertions of amino acids at A14-A15, A13-A14, A14-A19, and A14-B16 positions of the insulin molecule with tryptophan or other bulky residues such as naphthylalanine or Nγ-dansyl-a,γ-diaminobutyric acid or other hydrophobic amino acid residues such as leucine, valine, or phenylalanine also leads to hepatospecific insulins. Further modifications of the B chain moieties of the above mentioned insulin analogues at the B10 and B25 positions may be made in accordance with applicant's previous applications, U.S. Ser. Nos. 074,558 and 273,957, the disclosures of which are incorporated herein by reference. These additional substitutions yield superactive insulins believed to be hepatospecific.

The claimed insulin analogues can be produced by any of a variety of techniques known to those skilled in the art. For example, the component A and B chains of the insulin analogues can be synthesized by any of the known peptide synthesis techniques, including solid phase peptide synthesis techniques and solution techniques, e.g. fragment condensation. See, e.g. Erickson and Merrifield, *The Proteins* (1976), vol. 2, chapter 3, Academic Press, New York; Blake et al. Proc. Natl. Acad. Sci. (1983), vol. 80, pp. 1556–1559 for a discussion of peptide synthesis techniques. Some of the claimed insulin analogues can also be prepared by combining human or sheep B chain, isolated following reduction or oxidative sulfitolysis of intact pancreatic or recombinant insulin, with a modified A chain prepared by peptide synthetic techniques or recombinant DNA methods.

Recombinant DNA methods for producing the insulin A or B chains having substituted naturally-occurring amino acids at any position include, but are not limited to, cloning and expression of an in vitro synthesized DNA which codes for such an A or B chain amino acid sequence. Alternatively, an organism, such as bacteria, which expresses human insulin A or B chain could be induced to produce a modified chain by any of the techniques of in vitro site-directed mutagenesis. See e.g. Smith, Ann. Rev. Genet. (1985), vol. 19, pp. 423–463; Botstein et al. Science (1985), vol. 229, pp. 1193–1201.

In general, to prepare insulin having a modified A chain, sheep insulin B chains, obtained by any known technique are combined with the modified A chains prepared by any convenient technique. The B and modified A chains are preferably in their stabilized S-sulfonated forms which can then be recombined by known procedures to form the intact active insulin analogues. Known recombination techniques are taught by U.S. Pat. No. 3,420,810 to Katsoyannis and U.S. Pat. No. 4,421,685 to Chance et al. U.S. Pat. No. 4,421,685 provides a single step process for forming an insulin which involves bringing together an S-sulfonated A chain and S-sulfonated B chain in the presence of a thiol reducing agent, such as dithiothreitol or cysteine, in an aqueous medium. The conditions for recombination include (1) a pH of about 10.5, (2) a total protein concentration of about 0.1 to 50 mg/ml, and (3) a thiol reducing agent in a concentration which produces about 0.4 to 2.5 SH groups per each—S-SO$_3$ group present in the total A and B chain S-sulfonates present in the mixture. The formation of the insulin analogues occurs by maintaining the reaction at a temperature of about 0° to 5° C. in an environment which provides a source of oxygen to allow the formation of the insulin S-S bonds.

Once the recombination reaction has been completed, the insulin analogue can be isolated and assayed for purity and activity by a variety of techniques known to those skilled in the art. Commonly employed techniques for purification of insulin and insulin analogues are chromatographic techniques, such as high performance liquid chromatography (HPLC), gel filtration and ion-exchange chromatography. Purity of the product can be determined by a variety of techniques including inter alia HPLC, polyacrylamide gelelectrophoresis, amino acid analysis and amino acid sequencing.

Although insulin analogues, in general, maintain some residual insulin activity, the potency of such analogues is usually only a fraction of that of natural insulins. The potency of human, bovine and porcine insulins in USP standards is about 25-26 IU (international units) per mg protein. Standard assays for measuring insulin potency include inter alia (1) insulin radioreceptorassays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction, isolated rat adipocytes, or isolated rat hepatocytes; (2) lipogenesis assays, performed e.g. with rat adipocytes, in which relative insulin potency is defined as the ratio of insulin to insulin analogue required to achieve 50% of the maximum conversion of [3-$^3$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radioimmunoassays which can determine the immunogenicity of insulin analogues by measuring the effectiveness by which insulin or an insulin analogue competes with $^{125}$I-insulin in binding to specific anti-insulin antibodies; (5) inhibition of gluconeogenesis performed on confluent monolayers of a well differentiated hepatoma cell line (FAO) in which inhibition of glucose secretion into the medium is determined as a function of the concentration of insulin or insulin analogue. The relative potency of the analogue is defined as the ratio of the concentration of insulin to analogue required to produce half-maximal inhibition of glucose production; and (6) other assays which measure the binding of insulin or an insulin analogue to cells, such as cultured lymphocytes, known to possess specific insulin receptors.

The insulin analogues of the invention may also be formulated into pharmaceutical compositions for administration to diabetic patients. The pharmaceutical compositions comprise an insulin analogue according to the claimed invention in an amount which is therapeutically effective in promoting the attainment of hormonal homeostasis in the diabetic patient together with a pharmaceutically acceptable carrier. As with all insulin preparations for treatment of diabetes, adequate therapeutic amounts of the active compound to achieve hormonal homeostasis in individual patients must be determined. Factors to be considered include the severity of the diabetic condition and the route of administration of the composition. Ultimately the particular physician treating the diabetic patient has discretion in the amount of the pharmaceutical composition and route of administration. Natural insulins are generally given to a patient in a therapeutic dosage to afford about 0.02 to about 5 units of human insulin activity per kilogram body weight per day. See e.g. U.S. Pat. No. 4,652,547.

Pharmaceutical compositions containing a therapeutically effective amount of an insulin analogue according to the claimed invention may be administered parenterally to a diabetic patient in need of insulin treatment. Preferably the composition is administered intramuscularly, subcutaneously or intravenously. The composition may also be administered to the patient by nasal spray. Alternatively, for long-term controlled homeostasis, the composition may be incorporated into an implantable pump for administration to the patient. Such implantable devices which provide a controlled dosage of drug to a patient over a long period of time are known in the art. The composition additionally comprises a pharmaceutically acceptable carrier which must not be deleterious to the patient. The carrier must also not have any adverse effect on the active component of the composition, i.e., [Trp$^{14}$-A] insulin or another insulin analogue. Suitable carriers and other additives for pharmaceutical compositions which contain therapeutically effective amounts of the claimed insulin analogues as the active component may be found in U.S. Pat. No. 4,652,547 which provides for insulin-containing compositions.

As an example, the synthesis of [Trp$^{14}$-A] insulin was achieved by the interaction of S-sulfonated sheep B chain with S-sulfonated forms of [Trp$^{14}$] A chain (XX, below) of sheep insulin. The procedures described by Katsoyannis et al., *Biochemistry*, 6:2635-2642 (1967) and Chance et al., *Pept. Proc. Am. Pept. Symp. 7th*, 721-728 (1981) were followed. The synthesis of the A chain analogue involved, as the key step, the construction of the protected heneicosapeptide (XII below), containing the entire amino acid sequence of the respective A chain. For the construction of the protected heneicosapeptide either solid phase methodology according to Merrifield et al. *J. Am. Chem. Soc.*, 85, 2149-2154 (1963) and Merrifield et al., *Biochemistry*, 21, 5020-5031 (1982) or the fragment condensation approach was employed. The synthesis by the latter approach involved the coupling of the C-terminal pentapeptide (sequence A$^{17}$-A$^{21}$) with the adjacent pentapeptide (sequence A$^{12}$-A$^{16}$) to produce the C-terminal decapeptide (sequence A$^{12}$-A$^{21}$). The latter compound was coupled with the adjacent tripeptide (sequence A$^9$-A$^{11}$) to yield the C-terminal tridecapeptide (sequence A$^9$-A$^{21}$), which in turn was coupled with the adjacent tetrapeptide (sequence A$^5$-A$^8$) to produce the C-terminal heptadecapeptide (sequence A$^5$-A$^{21}$). The final coupling step involved the coupling of the C-terminal heptadecapeptide with the N-terminal tetrapeptide to yield the protected heneicosapeptide (XII or XIX, below). The usual blocking groups were employed for the protection of the secondary functions of the various amino acids (i.e., Bzl for Ser, Glu, Asn and Tyr and PMB for Cys) with the exception of the indole function of Trp, which was protected with the Mts group in accordance with Fujii et al., *Chem. Pharm. Bull. (Japan)* 32, 2660-2665 (1984). Removal of the blocking groups from the protected heneicosapeptide either with 1M trifluoromethanesulfonic acid - thioanisole in TFA containing m-cresole and EDT according to Yajima and Fujii, *J. Am. Chem. Soc.*, 103, 5867-5871 (1981) and Fujii et al., supra, using the modification described recently by Ogawa et al., *J. Protein Chem.*, 3, 327-348 (1984) or by the low/high hydrogen fluoride procedure according to Tam et al., *J. Am Chem. Soc.*, 105, 6442-6455 (1983) and sulfitolysis of the resulting reduced products yielded the S-sulfonated chain analogue XX.

The invention is further illustrated by the following specific examples which are not intended in any way to limit the scope of the invention.

EXAMPLE 1

Synthesis of Sheep [Trp$^{14}$-A] Insulin

A. Synthesis of A Chain

Boc-Gln-Leu•OMe (I)

To a solution of H•Leu•OMe, 11.3 g of HCl in DMF (50 mL) was added along with 9.1 mL of TEA followed by 17.6 g of Boc-Gln•ONp. After 24 hours the mixture was filtered and the filtrate concentrated to a small volume, under reduced pressure, and diluted with 500 mL of AcOEt and 100 mL water. The organic layer was washed with 1N NH$_4$OH, water, 0.5N HCl and water, dried and concentrated to dryness. The residue solidified on trituration with ether - petroleum ether and crystallized from ethyl acetate - ether: wt: 13.7 g (76.6%); mp: 126° C.; $[\alpha]_D^{25}$ −35.3° (c 1, methanol). Anal. Calcd. for C$_{17}$H$_{31}$N$_3$O$_6$: C, 54.7; H, 8.37; N, 11.3. Found: C, 55.0; H, 8.26; N, 11.3.

Z(OMe)-Trp(Mts)-Gln-Leu•OMe (II)

A solution of compound I (3.73 g) in TFA - anisole (8 mL - 2 mL) was stored at room temperature for 1.5 hours and concentrated to dryness under reduced pressure. The residue was triturated with a mixture of ether - petroleum ether (1:2, v/v) and dried over KOH in vacuo. A solution of this material in 20 mL of DMF containing 2.8 mL of TEA was cooled to 0° C. and was added to 6.21 g of the azide prepared from Z(OMe)-Trp-(Mts)-NHNH$_2$ according to Fujii et al., supra, following the method of Ogawa et al., supra. The following reagents were used in this reaction: DMF (20 mL), 6.3N HCl in DMF (3.5 mL), tert-butyl nitrate (1.5 mL) and TEA (3.1 mL). After 40 hours at 4° C. the mixture was diluted with AcOEt (600 mL) and saturated NaCl (100 mL). The organic layer was washed with 10% citric acid and saturated NaCl, dried and concentrated to dryness. Upon trituration with ether the residue solidified and then crystallized from ethanol: wt: 3.6 g (45%); mp: 171°-173° C.; $[\alpha]_D^{25}$ −41.4° (c 1, DMF). Anal. Calcd. for C$_{41}$H$_{51}$N$_5$O$_{10}$S: C, 61.1; H, 6.4; N, 8.7. Found: C, 61.0; H, 6.5; N, 8.5.

Boc-Leu-Trp(Mts)-Gln-Leu•OMe (III)

A solution of compound II (2.0 g) in a mixture of TFA - anisole - EDT (10 mL - 1 mL - 0.3 mL) was stored at 0° C. for 30 minutes and at room temperature for 30 minutes and then processed as described in the synthesis of compound II. 1.7 g of Boc-Leu•ONp was added to a solution of the resulting N$^\alpha$-deprotected peptide salt in DMF (35 mL) containing TEA (0.6 mL) cooled to 0° C. After 24 hours at room temperature the mixture was diluted with 600 mL of AcOEt, washed successively with 1N NH₄OH, saturated NaCl, 0.5N HCl and saturated NaCl, dried and concentrated to a small volume. The precipitated product was collected and recrystallized from AcOEt: wt: 1.51 g (71%); mp: 188°-190° C.; $[\alpha]_D^{25}$ −20.6° (c 1, DMF). Anal. Calcd. for $C_{43}H_{62}N_6O_{10}S$: C, 60.4; H, 7.3; N, 9.8. Found: C, 60.1; H, 7.5; N. 9.8. Amino acid analysis after 4M MSA hydrolysis gave the ratios: $Glu_{1.0}Leu_{2.0}Trp_{0.8}$.

Boc-Ser(Bzl)-Leu-Trp(Mts)-Gln-Leu-OMe (IV)

Deblocking of compound III (4.46 g) with TFA -anisole - EDT (15 mL - 1.2 mL - 0.8 mL) and isolation of the resulting $N^\alpha$-deprotected peptide salt was carried out as described in the synthesis of compound III. 2.07 g of Boc-Ser(Bzl)•OH was added at 0° C. to a solution of this material in DMF (60 mL) containing TEA (1.1 mL), followed by addition of 1.65 g of N, N'-dicyclohexylcarbodiimide and 1.08 g of 1-hydroxybenzotriazole. After 24 hours at room temperature the urea by-product was filtered off and the filtrate diluted with 600 mL AcOEt and saturated with 100 mL of NaCl. The organic layer was washed as usual, dried and concentrated to a small volume. The precipitated product was collected and reprecipitated from ethyl acetate - ether: wt: 4.58 g (85%); mp: 187°-188° C.; $[\alpha]_D^{25}$ −21.6° (c 1, DMF). Anal. Calcd. for $C_{53}H_{73}N_7O_{12}S$: C, 61.7; H, 7.1; N, 9.5. Found: C, 61.4; H, 7.2; N, 9.3. Amino Acid analysis after 4M MSA hydrolysis gave the ratios: $Ser_{1.0}Glu_{1.0}Leu_{2.0}Trp_{0.7}$.

Boc-Ser(Bzl)-Leu-Trp(Mts)-Gln-Leu-NHNH₂ (V)

A solution of compound IV (4.2 g) in a mixture of DMF (35 mL) and ethanol (10 mL) containing hydrazine hydrate (1.0 mL) was stored at room temperature for 24 hours and then diluted with 200 mL of 50% aqueous ethanol. The precipitate product was collected and reprecipitated from methanol - water: wt: 4.0 g (94%); mp: 203°-205° C.; $[\alpha]_D^{25}$ −6.1° (c 1, DMSO) Anal. Calcd. for $C_{52}H_{73}N_9O_{11}S$: C, 60.5; H, 7.1; N, 12.2. Found: C, 60.9; H, 7.4; N, 12.0. A 4M MSA hydrolysate gave the ratios: $Ser_{0.9}Glu_{1.0}Leu_{2.0}Trp_{0.7}$.

Boc-Tyr(Bzl)-Cys(PMB)-Asn•OBzl (VI)

A solution of 7.39 g of Boc-Cys-(PMB)-Asn•OBzl prepared according to Ohta et al., *J. Protein Chem.*, 7, 55–65 (1988) in TFA - anisole (15 mL - 3 mL) was stored at 0° C. for 30 minutes and at room temperature for 1.5 hours and then concentrated under reduced pressure. The residue was triturated with a mixture of ether and petroleum ether (1:1 v/v) and dried over KOH in vacuo. 7 g of Boc-Tyr(Bzl)•ONp was added to a solution of this material in DMF (60 mL) containing TEA (2.3 mL) and cooled to 0° C. After 24 hours at room temperature the mixture was diluted with 600 mL of AcOEt and 100 mL of 1N NH₄OH. The organic phase was washed (1N NH₄OH, 0.5N HCl and water), dried and concentrated to a small volume. The precipitated product was collected and recrystallized from AcOEt: wt: 8.7 g (84%); mp: 174°-175° C.; $[\alpha]_D^{25}$ −18.6° (c 1, DMF). Anal. Calcd. for $C_{43}H_{50}N_4O_9S$: C, 64.6; H, 6.30; N, 7.0. Found: C, 64.0; H, 6.35; N, 7.0.

Boc-Asn-Tyr(Bzl)-Cys(PMB)-Asn•OBzl (VII)

8.2 g of compound VI was deblocked with TFA - anisole (22 mL - 2.2 mL) as described above. Trituration of the residue with ether caused the precipitation of the $N^\alpha$-deprotected peptide salt which was filtered off and dried over KOH in vacuo. 3.9 g of Boc-Asn•ONp was added to a solution of this product in DMF (50 mL) containing TEA (1.8 mL) and cooled to 0° C. After 24 hours at room temperature the reaction mixture was diluted with 200 mL of methanol and the precipitated product was filtered off, washed (1N NH₄OH, 0.5N HCl and water), dried and reprecipitated from DMF - methanol: wt: 6 g (64%); mp: 237°-238° C.; $[\alpha]_D^{25}$ −37.4° (c 1, DMF). Anal. Calcd. for $C_{47}H_{56}N_6O_{11}S$: C, 61.8; H, 6.18; N, 9.2. Found: C, 61.6; H, 6.30; N, 9.1.

Boc-Glu(OBzl)-Asn-Tyr(Bzl)-Cys(PMB)-Asn•OBzl (VIII)

The deblocking of compound VII (5.5 g) and isolation of the $N^\alpha$-deprotected peptide salt was carried out as described in the synthesis of compound VII. 3.3 g of Boc-Glu-(OBzl)•ONp (prepared from the method of Sandrin et al., *Helv. Chim. Acta*, 46: 1637–1669 (1963)) was added to a solution of this product in DMF (50 mL) containing TEA (0.85 mL) at 0° C. The reaction mixture was processed as in the synthesis of compound VII: wt: 5.6 g (81%); mp: 206°-207° C.; $[\alpha]_D^{25}$ −41.4° (c 1, DMF). Anal. Calcd. for $C_{59}H_{69}N_7O_{14}S$: C, 62.6; H, 6.14; N, 8.7. Found: C, 62.3; H, 5.94; N, 8.5. Amino acid ratios in a 6N HCl hydrolysate: $Asp_{1.8}Glu_{1.0}Tyr_{1.0}$. Cys(PMB) was not determined.

Boc-Ser(Bzl)-Leu-Trp(Mts)-Gln-Leu-Glu(OBzl)-Asn-Tyr(Bzl)-Cys(PMB)-Asn•OBzl (IX)

The deblocking of compound VIII (2.3 g) and isolation of the $N^\alpha$-deprotected peptide salt was carried out as described in the synthesis of compound VII. 2.98 g of the azide prepared from compound V (according to Ogawa et al., supra) was added to a solution of this product in DMF (35 mL) containing TEA (0.42 mL) and cooled to 0° C. The reagents used for this reaction were as follows: DMF (20 mL), 6.3N HCl in DMF (0.92 mL), tert-butyl nitrite (0.42 mL) and TEA (0.98 mL). After 48 hours at 4° C. the reaction mixture was diluted with AcOEt (20 mL) and 5% citric acid (100 mL) and the precipitated product was filtered off, washed with water and methanol and reprecipitated from DMF - methanol: wt: 1.55 g (38%), mp: 245°-246° C.; $[\alpha]_D^{25}$ −15.7° (c 1, DMSO). Anal. Calcd. for $C_{106}H_{131}N_{14}O_{23}S_2$•2H₂O: C, 61.5; H, 6.6; N, 9.5. Found: C, 61.4; H, 6.5; N, 9.7. Amino acid ratios in a 6N HCl hydrolysate: $Asp_{2.0}Ser_{0.9}Glu_{2.1}Leu_{2.1}Tyr_{1.0}$. Trp and Cys(PMB) were not determined.

Boc-Gly-Val-Cys(PMB)-Ser(Bzl)-Leu-Trp(Mts)-Gln-Leu-Glu(OBzl)-Asn-Tyr(Bzl)-Cys(PMB)-Asn•OBzl (X)

A solution of compound IX (0.95 g) in TFA - anisole - EDT (5 mL - 0.11 mL - 0.08 mL) was stored at 0° C. for 30 minutes and at room temperature for 1.5 hours. The excess TFA was removed by evaporation under reduced pressure and the residue triturated with ether. The precipitate formed was filtered off and dried over KOH In vacuo. 0.82 g of the azide prepared from Boc-Gly-Val-Cys(PMB)-NHNH₂ according to Ogawa et al., supra, was added to a solution of this product in DMF (25 mL) containing TEA (0.09 mL). The reagents used for this reaction were was follows: DMF (10 mL), 6.3N HCl in DMF (0.51 mL), tert-butyl nitrite (0.24 mL) and TEA (0.49 mL). After 48 hours at 4° C. the reaction mixture was diluted with AcOEt (20 mL) and 5% citric acid (60 mL) and the precipitated product was collected and reprecipitated from DMF - methanol: wt: 0.93 g (82%); mp: 267°-268° C.; $[\alpha]_D^{25}$ −17.4° (c 1, DMSO). Anal. Calcd. for $C_{124}H_{156}N_{17}O_{27}S_3$•3H₂O: C, 60.4; H, 6.6; N, 9.7. Found: C, 60.3; H, 6.4; N, 9.9. Amino acid ratios in a 6N HCl hydrolysate: $Asp_{1.9}Ser_{0.9}Glu_{2.0}$.

$Gly_{1.0}Val_{1.0}Leu_{2.1}Tyr_{0.9}$. Trp and Cys (PMB) were not determined.

Boc-Gln-Cys(PMB)-Cys(PMB)-Ala-Gly-Val-Cys(PMB)-Ser(Bzl)-Leu-Trp(Mts)-Gln-Leu-Glu(OBzl)-Asn-Tyr(Bzl)-Cys(PMB)-Asn•OBzl (XI)

The deblocking of compound X (0.82 g) with TFA - anisole - EDT (5 mL - 0.5 mL - 0.1 mL) and the isolation of the $N^\alpha$-deprotected peptide salt was carried out as described above. 1.06 g of the azide prepared from Boc-Gln-Cys(PMB)-Cys(PMB)-Ala-NHNH$_2$ according to Ogawa et al., supra, was added to a solution of this product in DMF (40 mL) containing TEA (0.1 mL). The reagents used for this reaction were as follows: DMF (20 mL), 6.3N HCl in DMF (0.43 mL), tert-butyl nitrite (0.21 mL) and TEA (0.42 mL). After 48 hours at 4° C. the reaction mixture was diluted with 200 mL of methanol and the precipitated heptadecapeptide derivative was collected and reprecipitated from DMF - methanol: wt: 0.85 g; mp: >270° C.; $[\alpha]_D^{25}$ −21.4° (c 1, DMSO). Amino acid ratios in a 6N HCl hydrolysate are as follows: $Asp_{2.0}Ser_{0.9}Glu_{3.1}$-$Gly_{1.0}Ala_{1.2}Val_{0.9}Leu_{1.9}Tyr_{0.7}$. Trp and Cys(PMB) were not determined.

Z-Gly-Ile-Val-Glu(OBu$^t$)-Gln-Cys(PMB)-Cys(PMB)-Ala-Gly-Val-Cys(PMB)-Ser(Bzl)-Leu-Trp(Mts)-Gln-Leu-Glu(OBzl)-Asn-Tyr(Bzl)-Cys(PMB)-Asn•OBzl (XII)

The deblocking of compound XI (0.6 g) with TFA - anisole - EDT (6 mL - 0.6 mL - 0.1 mL) and the isolation of the resulting product was carried out as described above. 0.49 g of the azide prepared from Z-Gly-Ile-Val-Glu(OBu$^t$)-NHNH$_2$ (prepared with the method of Katsoyannis et al., *J. Am. Chem. Soc*, 88:5622–5625 (1966) was added to a solution of this material in DMF (40 mL) containing TEA (0.06 mL). The reagents used for this reaction were as follows: DMF (20 mL), 6.3N HCl in DMF (0.25 mL), tert-butyl nitrite (0.11 mL) and TEA (0.3 mL). After 48 hours at 4° C., the reaction mixture was diluted with methanol (200 mL) and the precipitated protected heneicosepeptide was collected and reprecipitated from DMF - methanol: wt: 0.53 g (76%); mp: >270° C. Amino acid analysis after 6N HCl-hydrolysis gave the following molar ratios: $Asp_{2.0}Ser_{0.9}Glu_{4.0}Gly_{2.1}Ala_{1.0}$ $Val_{1.5}Ile_{0.6}Leu_{1.8}Tyr_{0.7}$. Trp and Cys(PMB) were not determined.

B. Synthesis of S-Sulfonated [Trp$^{14}$] A Chain (XX)

Figure 1:
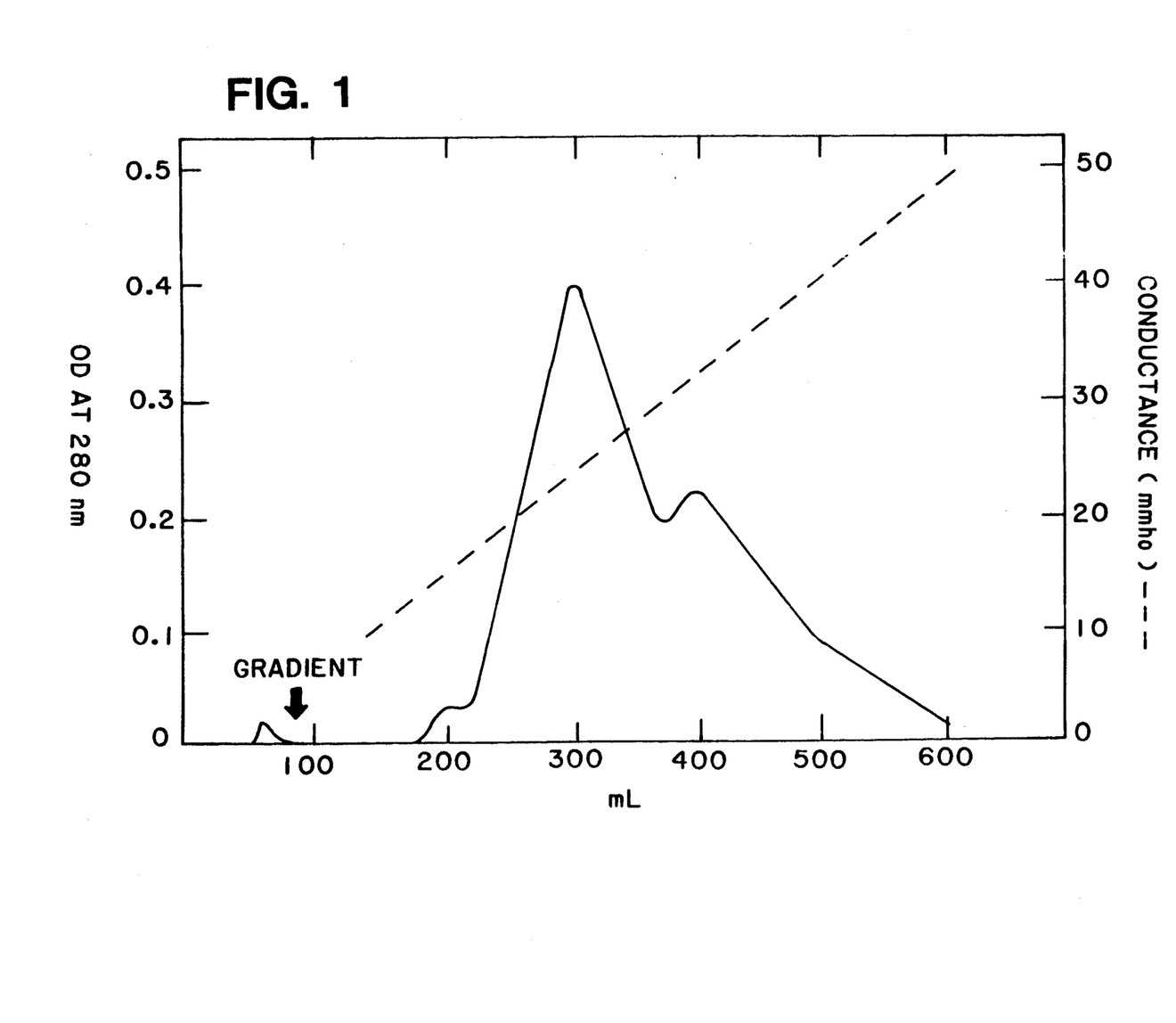
FIG. 1 is a chromatogram showing the elution of crude sheep [Trp$^{14}$] A chain S-sulfonate from a Cellex-E column (200-350 ml of effluent).

The protected heneicosapeptide XII (200 mg) was treated with 1M trifluoromethanesulfonic acid in TFA (4.3 mL) containing thioanisole (0.66 mL), m-cresole (0.59 mL) and EDT (0.47 mL) at 0° for 2 hours. This solution was then cooled to −10° C., and 8M guanidine hydrochloride (25 mL) containing concentrated NH$_4$OH (5 mL) was added dropwise and with vigorous stirring. During this process, the temperature of the mixture was kept below 5° C. The resulting mixture (pH ~5) was extracted 3 times with ether (50 mL each), and to the aqueous layer, adjusted to pH 8.9 with NH$_4$OH, were added 1.2 g of sodium sulfite and 0.6 g of sodium tetrathionate. The mixture was stirred at room temperature for 3.5 hours, then placed in Spectrapor membrane tubing No. 3 and dialyzed against four changes of distilled water (4 L each) at 4° C. for 24 hours. Lyophilization of the dialysate afforded the crude S-sulfonated chain analogue which was dissolved in 6 mL of 0.015M NH$_4$HCO$_3$ and chromatographed on a Sephadex G-15 column (4.2×45 cm), equilibrated and eluted with 0.015M NH$_4$HCO$_3$. The effluent corresponding to the main peak, as monitored with an ISCO spectrophotometer, was lyophilized and the sheep insulin [Trp$^{14}$] A chain S-sulfonate was obtained as a white powder: wt: 130.5 mg. For purification, this material (71.3 mg) was dissolved in 0.1M Tris-HCL buffer (pH 7.0; 3 mL) and applied on a Cellex-E column (1.2×43 cm), which was equilibrated with the same buffer. Elution of the column was carried out with Tris-HCl buffer (pH 7.0) and a linear NaCl gradient as described previously by Chu et al., *Biochemistry*, 26, 6966–6971 (1987). The chromatographic pattern, as monitored with an ISCO spectrophotometer and a conductivity meter (Radiometer, Copenhagen), is shown in FIG. 1. The effluent corresponding to the main peak (230–360 mL) was collected, dialyzed as above and lyophilized: wt: 35.4 mg.

Amino acid analysis of the synthetic chain analogue was performed in two acid hydrolysates; one using 6N HCl and another using 4M MSA (for Trp determination) as in the method of Simpson et al., *J. Biol. Chem.*, 251, 1936–1940 (1976). The amino acid composition, expressed in molar ratios, was in agreement with the theoretically expected values. Digestion of the synthetic chain analogue with aminopeptidase M and amino acid analysis of the digest gave the expected molar ratios. The synthetic material was completely digested by the enzyme indicating that the stereochemical purity of the constituent amino acids was preserved during the synthetic processes.

C. Synthesis and Isolation of Sheep [Trp$^{14}$-A] Insulin

Figure 2A:
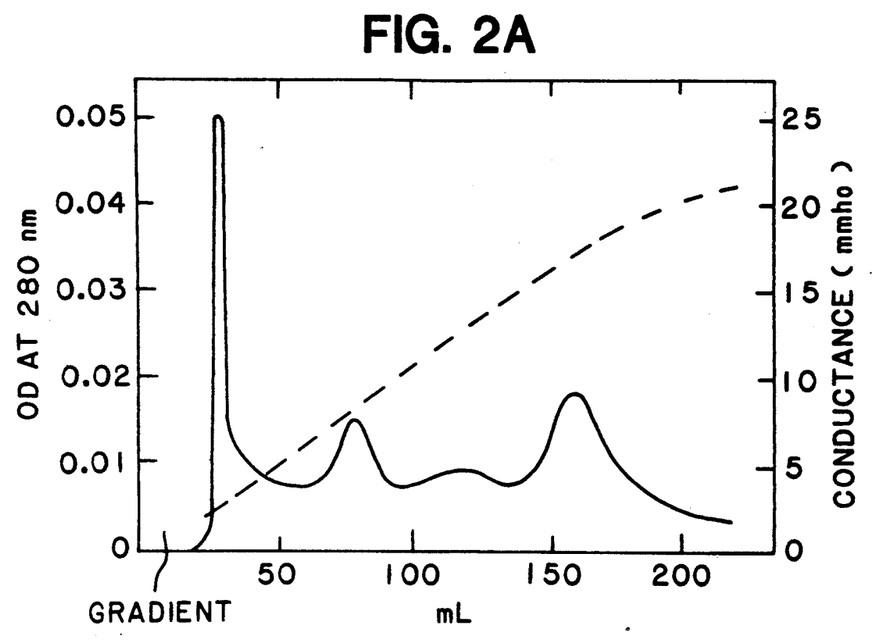
FIG. 2A is a chromatogram showing the elution of a mixture of sheep B chain S-sulfonate and sheep [Trp$^{14}$] A chain S-sulfonate at the initial chromatographic separation from a CM-cellulose column.
Figure 2B:
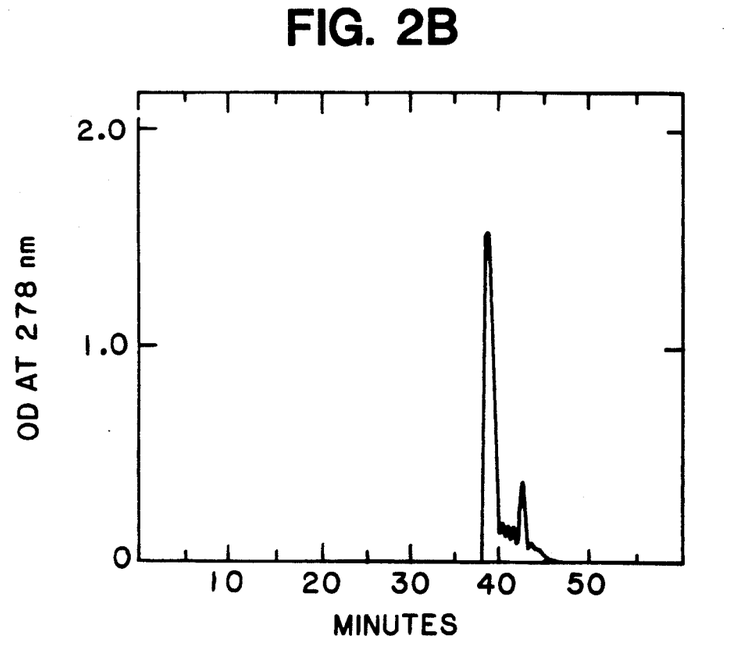
FIG. 2B is a reversed-phase HPLC chromatogram showing the rechromatography of the material in the peak shown in FIG. 2A (140-180 ml of effluent).

The synthesis of sheep [Trp$^{14}$-A] insulin was carried out by the interaction of the S-sulfonated [Trp$^{14}$] sheep A chain (XX) with the S-sulfonated sheep (which is the same as bovine) B chain in the presence of dithiothreitol following the method of Chance et al., supra. A solution of sheep B chain S-sulfonate (10 mg) (prepared as described by Katsoyannis et al., *Biochemistry*, 6, 2635–2642 (1967)), [Trp$^{14}$] A chain S-sulfonate (20 mg) and dithiothreitol (6.83 mg) in 0.1M glycine buffer (pH 10.5, 6 mL) was stirred at 4° C. for 24 hours and then processed as described previously by Katsoyannis et al., *Biochemistry*, 6, 2656–2668 (1967). Isolation and purification of the insulin analogue from the combination mixture were carried out by chromatography on a CM-cellulose column (0.9×24 cm) with an acetate buffer (Na+, 0.024M, pH 3.3) and an exponential NaCl gradient as described by Katsoyannis et al., supra. The elution pattern obtained, as monitored by an ISCO spectrophotometer and a conductivity meter (Radiometer, Copenhagen), is shown in FIG. 2A. 1.3 mg of the [Trp$^{14}$-A] insulin was isolated from the effluent (145–175 mL) via picrate as the hydrochloride in accordance with Katsoyannis et. al., supra. Final purification of this material was accomplished by reversed-phase HPLC on a Vydac ® 218 TP column (0.45×25 cm) connected to an LKB liquid chromatography system. Chromatography was carried out at a flow rate of 0.5 mL/min with a 10–50% linear gradient of 2-propanol in 0.1% TFA over 60 minutes (FIG. 2B). Lyophilization of the effluent under the main peak achieved the sheep [Trp$^{14}$-A] insulin in a highly purified form.

Amino acid analysis of the synthetic material, after 6N HCl hydrolysis, gave a composition expressed in molar ratios in good agreement with the theoretically expected values.

EXAMPLE 2

Analysis of [Trp$^{14}$-A] Insulin Potency And Binding Properties

In this Example the materials used and the analytical procedures followed are those found in Kitagawa et al., *Biochemistry*, 23: 1405–1413 (1984). $^{125}$I-insulin for receptor binding studies and [3-$^3$H] glucose for lipogenesis were obtained from DuPont NEN Research Products. Cellulose acetate membrane filters, 0.2 μm pore size, were products of Sartorius. Glass-fiber filters, Type GFC, were from Whatman. Collagenase, Type II crude, was obtained from Worthington. The scintillation fluids Filtron-X ®, Hydrofluor ® and Soluscint-O ® were products of National Diagnostics. Crystalline bovine insulin was from Sigma, and fatty-acid free bovine serum albumin from Boehringer - Mannheim Biochemicals.

A. Insulin Receptor Binding Assay

The ability of [Trp$^{14}$-A] insulin to inhibit the specific binding of $^{125}$I-insulin to insulin receptors was examined in a fraction of rat liver enriched in plasma membranes, isolated rat adipocytes, and isolated rat hepatocytes. The first two procedures were done in accordance with Burke et. al, *Biochemistry* 19:4547–4556, (1980).

Briefly, triplicate 0.2 ml incubations contained $^{125}$I-insulin, $3 \times 10^{-10}$M, unlabelled insulin or [Trp$^{14}$-A] insulin prepared as in Example 1, and plasma membranes (20–40 μg of protein) in 0.1M sodium phosphate, pH 7.4, containing 0.6% fraction V bovine serum albumin. Following incubation for 45 min at 24° C., the mixtures were diluted with 2.0 ml of ice cold 0.1M sodium phosphate, pH 7.4, containing 0.1% fraction V bovine serum albumin and immediately filtered through cellulose-acetate filters. The filters were washed twice with the ice cold buffer, dried, and then radioactivity was counted in a scintillation counter using Filtron-X ®. Relative potency was obtained as the concentration ratio of unlabelled insulin to [Trp$^{14}$-A] insulin required to inhibit 50% of the specific binding of $^{125}$I-insulin to the receptor preparation. In this assay [Trp$^{14}$-A] insulin displayed a potency of about 60% of that of the natural hormone.

B. Lipogenesis Assay

These assays measured the ability of the insulin analogue as compared to bovine insulin to convert [3-$^3$H] glucose into lipids.

Adipocytes were prepared by incubating epididymal and perirenal fat pads obtained from male rats weighing 200–300 g with 1.0 mg/ml collagenase for 60 min at 37° C., followed by filtration through gauze and then through fine-mesh silk. Cells were washed twice by flotation in a clinical centrifuge before suspension for use. The incubation medium was KrebsRinger bicarbonate containing half the recommended calcium, 0.5 mM glucose, and 3% fatty acid free bovine serum albumin, with 95% $O_2$-5% $CO_2$ as the gas phase. Triplicate lipogenesis incubations contained 1.0 ml of adipocyte suspension (20–40 mg dry wt cells) and bovine insulin or [Trp$^{14}$-A] insulin, prepared as in Example 1. Cells were preincubated for 45 min at 37° C. before the addition of [3-$^3$H] glucose. Incubation was continued for 60 min and stopped by the addition of 0.2 ml of 5N $H_2SO_4$ and 0.2 ml of corn oil to aid in the extraction of lipids. Samples were extracted with 10 ml of Soluscint-0 ® for 30 min at room temperature before counting the radioactivity in a scintillation counter. Under these conditions, [3-$^3$H] glucose was not extracted into the organic phase containing the scintillation fluors and was essentially uncounted. Zero and 100% stimulation of lipogenesis were defined as radioactivity observed in the absence and presence, respectively, of $9.1 \times 10^{-10}$M insulin (5.5 ng/ml). Relative potency was obtained as the concentration ratio of insulin to [Trp$^{14}$-A] insulin required to produce 50% of the maximum stimulation of lipogenesis.

Figure 3:
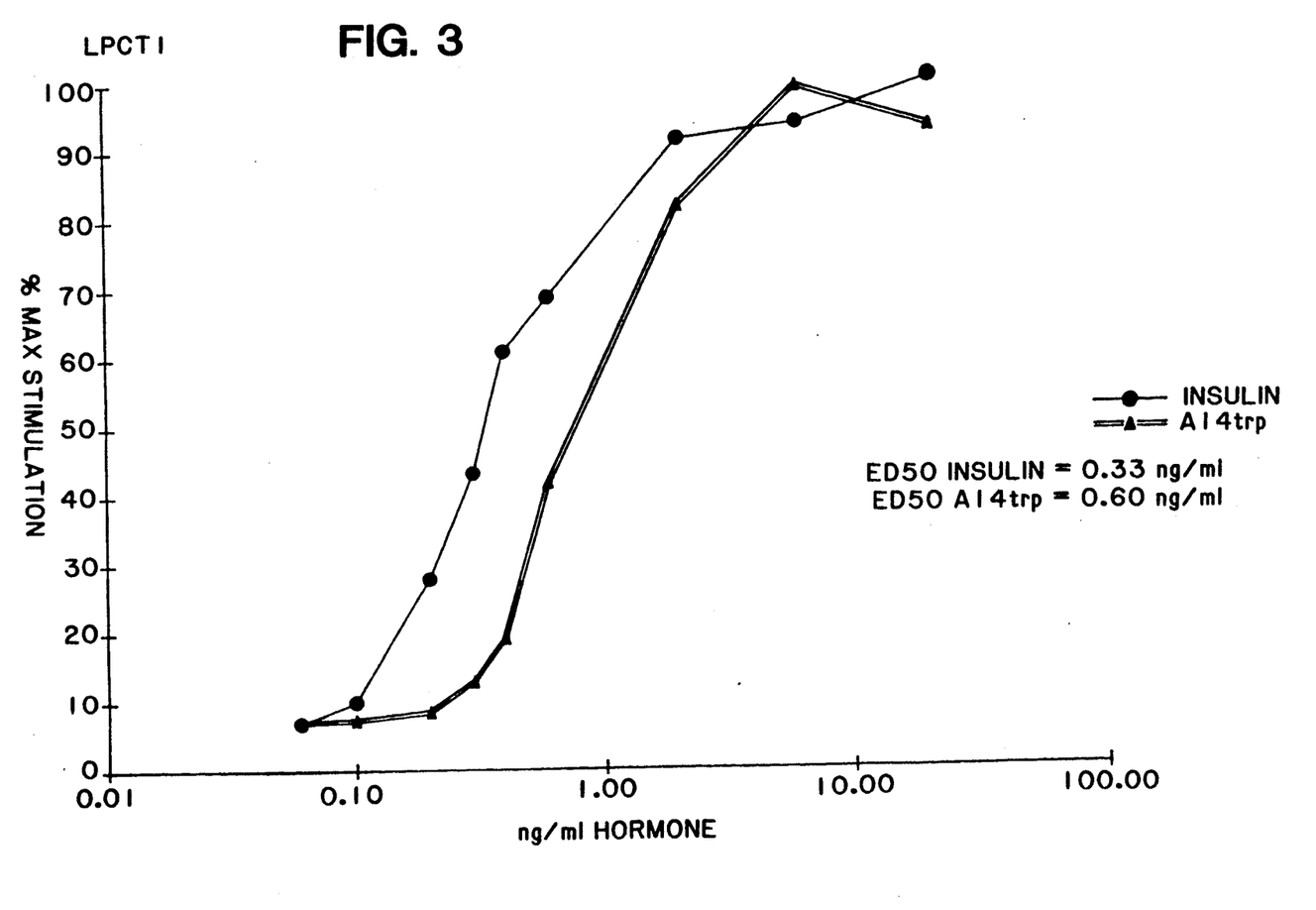
FIG. 3 is a graph comparing the stimulation of lipogenesis in rat adipocytes by natural insulin and [Trp$^{14}$-A] insulin.

FIG. 3 shows the stimulation of [3-$^3$H] glucose into organic-extractable material (i.e., lipids) in isolated rat adipocytes by [Trp$^{14}$-A] insulin (=▲=) as prepared in Example 1 and bovine insulin (-●-). Stimulation, expressed a percent of maximum, was plotted as a function of the agonist concentration. The data points represent the mean triplicate determinations in representative assays performed four times.

For both insulins the same maximum stimulation of lipogenesis was observed and half-maximal stimulation was produced by about twice the concentration of agonist. The potency of the synthetic insulin in lipogenesis (approximately 60% compared to the natural hormone) thus reflects its behavior in receptor binding assays employing adipocytes.

C. Inhibition of Gluconeogenesis Assay

This assay was carried out on confluent monolayers of a well differentiated hepatoma cell line (Lauris et al. *Endocrinology* 118:2519–2524 (1986)) in which glucose production was monitored with a commercial glucose oxidase kit (Sigma kit no. 510-A, Sigma Technical Bulletin 510, 1983). Inhibition of glucose secretion into the medium was determined as a function of the concentration of insulin or insulin analogue, and the relative potency of the analogue was defined as the ratio of the concentration of insulin to analogue required to produce half-maximal inhibition of glucose production. The cell culture and glucose production was carried out as described by Lauris et al., supra.

Figure 4:
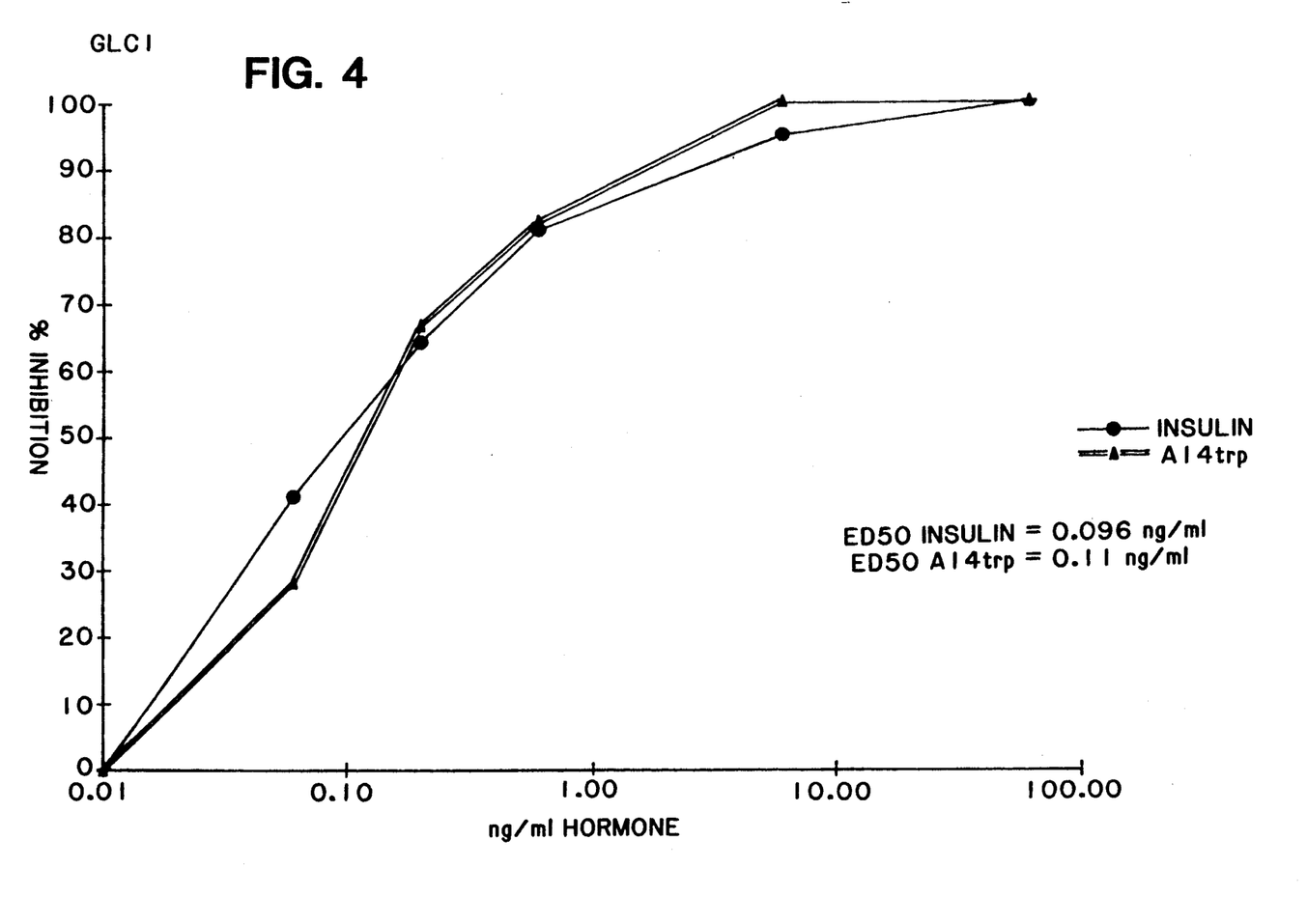
FIG. 4 is a graph comparing the inhibition of gluconeogenesis in FAO cells in which inhibition of glucose secretion is determined as a function of natural insulin or [Trp$^{14}$-A] insulin.

FIG. 4 shows the inhibition of gluconeogenesis in FAO cells, expressed as a per cent of maximum, and is presented as a function of insulin (-●-) and [Trp$^{14}$-A] insulin (=▲=) concentration. For both insulins the same maximum inhibition of gluconeogenesis was observes and half-maximal inhibition was produced by approximately the same concentration of agonist. The potency of the synthetic insulin in inhibiting gluconeogenesis is calculated to be about 90% relative to the natural hormone.

I claim:

1. An analogue of a naturally occurring insulin having an A chain comprising amino acids A1 through A21 and a B chain comprising amino acids B1 through B30, in which analogue the A14 amino acid is substituted with an amino acid residue selected from the group consisting of tryptophan, naphtylalanine, Nγ-dansyl-a, γ-diaminobutyric acid, leucine, valine, alanine, isoleucine, proline, and methionine, said insulin analogue otherwise being sufficiently structurally similar to natural insulin so as to retain at least some therapeutically effective portion of insulin potency.

2. An analogue of a naturally occurring insulin having an A chain comprising amino acids A1 through A21 and a B chain comprising amino acids B1 through B30, in which analogue tryptophan is substituted in the A chain for an amino acid selected from the group consisting of the A13 amino acid, the A14 amino acid, and combinations thereof, said insulin analogue otherwide being sufficiently structurally similar to natural insulin so as to retain at least one therapeutically effective portion of insulin potency.

3. An insulin analogue having the formula

4. A pharmaceutical composition for the treatment of diabetes in a patient in need of such treatment comprising a therapeutically effective amount of an insulin analogue according to claims 1, 2, or 3 together with a pharmaceutically acceptable carrier.

5. The pharmaceutical composition according to claim 4 for intramuscular administration.

6. The pharmaceutical composition according to claim 4 for subcutaneous administration.

7. The pharmaceutical composition according to claim 4 for intravenous administration.

8. The pharmaceutical composition according to claim 4 for administration by implantable pump.

9. The pharmaceutical composition according to claim 4 for administration by nasal spray.

10. A method of treating diabetes in a patient in need of such treatment comprising administering to the patient a therapeutically effective amount of an insulin analogue according to claims 1, 2, or 3 together with a pharmaceutically acceptable carrier.

11. The method according to claim 10, wherein the insulin analogue is administered intramuscularly.

12. The method according to claim 10, wherein the insulin analogue is administered subcutaneously.

13. The method according to claim 10, wherein the insulin analogue is administered intravenously.

14. The method according to claim 10 wherein the insulin analogue is administered by an implantable pump.

* * * * *

UNITED STATES PATENT AND TRADEMARK OFFICE
CERTIFICATE OF CORRECTION

PATENT NO. : 5,208,217  Page 1 of 2

DATED : May 4, 1993

INVENTOR(S) : Panayotis G. Katsoyannis

It is certified that error appears in the above-identified patent and that said Letters Patent is hereby corrected as shown below:

Col. 3, line 5, "difficultly" should read --difficulty--;

Col. 4, line 25, that portion of the formula reading "H-Glu" should read --H-Gly--;

Col. 10, line 59 "were was" should read --were as--;

Col. 11, line 40, "heneicosepeptide" should read --henricosapeptide--;

Col. 11, line 67, "eluded" should read --eluted--;

Col. 14, bridging lines 14-15, "expressed a" should read --expressed as a--;

Col. 14, bridging lines 46-47, "observes" should read --observed--;

Col. 15, line 2, "otherwide" should read --otherwise--;

Col. 15, line 4, "one" should read --some--; and

UNITED STATES PATENT AND TRADEMARK OFFICE
CERTIFICATE OF CORRECTION

PATENT NO. : 5,208,217
DATED : May 4, 1993
INVENTOR(S) : Panayotis G. Katsoyannis It is certified that error appears in the above-indentified patent and that said Letters Patent is hereby corrected as shown below:

Col. 15, line 8, that portion of the formula reading "H-Glu" should read-- H-Gly--.

Signed and Sealed this

Seventh Day of June, 1994

Attest:

BRUCE LEHMAN

Attesting Officer

Commissioner of Patents and Trademarks